(12) United States Patent
Destoumieux et al.

(10) Patent No.: US 9,955,954 B2
(45) Date of Patent: May 1, 2018

(54) TOOL FOR COLLECTING A SAMPLE OF ANIMAL TISSUE

(75) Inventors: Jean-Jacques M. Destoumieux, Lesure-D'Albigeois (FR); Bruno M. Teychene, Mouzieys-Teulet (FR)

(73) Assignee: Allflex Europe (FR)

( * ) Notice: Subject to any disclaimer, the term of this patent is extended or adjusted under 35 U.S.C. 154(b) by 404 days.

(21) Appl. No.: 13/702,899

(22) PCT Filed: Jun. 9, 2011

(86) PCT No.: PCT/EP2011/059636
§ 371 (c)(1),
(2), (4) Date: Apr. 12, 2013

(87) PCT Pub. No.: WO2011/154510
PCT Pub. Date: Dec. 15, 2011

(65) Prior Publication Data
US 2013/0204159 A1    Aug. 8, 2013

(30) Foreign Application Priority Data

Jun. 9, 2010  (FR) ..................... 10 54563

(51) Int. Cl.
*A61B 10/02*    (2006.01)
*A01K 11/00*    (2006.01)
*A61B 10/00*    (2006.01)

(52) U.S. Cl.
CPC ........ *A61B 10/0266* (2013.01); *A01K 11/003* (2013.01); *A61B 10/0096* (2013.01)

(58) Field of Classification Search
CPC .... A01K 11/00; A01K 11/002; A01K 11/003; A61B 10/02; A61B 10/0233; A61B 10/0266; A61B 2017/32004
(Continued)

(56) References Cited

U.S. PATENT DOCUMENTS 42,188 A     4/1864  Hamilton
1,347,868 A  7/1920  Nichols
(Continued)

FOREIGN PATENT DOCUMENTS

EP    1014861 A1    7/2000
EP    1024354 A1    8/2000
(Continued)

OTHER PUBLICATIONS

Translation. (1992). In C. Morris (Ed.), Academic press Dictionary of science and technology. Oxford, United Kingdom: Elsevier Science & Technology. Retrieved from <http://search.credoreference.com/content/entry/apdst/translation/0> on Feb. 23, 2016.*
(Continued)

*Primary Examiner* — David J McCrosky
(74) *Attorney, Agent, or Firm* — KPPB LLP

(57) ABSTRACT

The invention relates to a tool for collecting a sample of animal tissue, for interacting with collection mechanism including at least one cutting element capable of cutting out a sample and a pushing element movable with respect to the cutting element and capable of pushing the sample into post-cutting storage area. According to the invention, such a tool includes: a mechanism for driving the cutting element (21), a mechanism for driving the pushing element (23), and a mechanism for reversibly coupling the drive mechanism of the cutting element with the drive mechanism of the pushing element.

8 Claims, 11 Drawing Sheets

(58) Field of Classification Search
USPC ........ 600/564, 562, 567; 606/184, 185, 116, 606/117; 604/198; 119/858–862, 655
See application file for complete search history.

(56) References Cited

U.S. PATENT DOCUMENTS

| | | | |
|---|---|---|---|
| 2,570,048 A * | 10/1951 | Cooke et al. ................. 227/15 | |
| 2,617,359 A | 11/1952 | Horn et al. | |
| 2,749,566 A | 6/1956 | Thomas | |
| 3,731,414 A | 5/1973 | Murphy et al. | |
| 3,893,813 A | 7/1975 | Johnson et al. | |
| 3,952,438 A | 4/1976 | Propst | |
| 4,014,748 A | 3/1977 | Spinner et al. | |
| 4,021,952 A | 5/1977 | Brierley | |
| 4,185,635 A * | 1/1980 | Burford ............... A01K 11/002 606/117 | |
| 4,206,757 A | 6/1980 | Grandadam et al. | |
| 4,359,015 A | 11/1982 | Ritchey | |
| 4,425,874 A | 1/1984 | Child | |
| 4,653,208 A | 3/1987 | Wassilieff et al. | |
| 4,694,781 A | 9/1987 | Howe et al. | |
| 4,878,456 A | 11/1989 | Howe | |
| 4,885,855 A | 12/1989 | Marks et al. | |
| 4,932,953 A | 6/1990 | Cohr | |
| 5,005,433 A * | 4/1991 | Patton ..................... G01N 1/08 73/863 | |
| 5,016,369 A | 5/1991 | Parry | |
| 5,156,160 A * | 10/1992 | Bennett ..................... 600/567 | |
| 5,189,986 A | 3/1993 | Burkoth | |
| 5,268,148 A | 12/1993 | Seymour | |
| 5,388,588 A | 2/1995 | Nabai et al. | |
| 5,423,793 A | 6/1995 | Isono et al. | |
| 5,482,008 A | 1/1996 | Stafford et al. | |
| 5,526,822 A | 6/1996 | Burbank et al. | |
| 5,902,280 A | 5/1999 | Powles et al. | |
| 6,070,593 A | 6/2000 | Chase | |
| 6,080,173 A | 6/2000 | Williamson et al. | |
| 6,098,324 A | 8/2000 | Nepote | |
| 6,145,225 A | 11/2000 | Ritchey | |
| 6,164,501 A | 12/2000 | Stradella | |
| 6,196,978 B1 | 3/2001 | Weilandt et al. | |
| 6,255,101 B1 | 7/2001 | Rousseau et al. | |
| 6,382,827 B1 | 5/2002 | Gebrian | |
| 6,509,187 B2 | 1/2003 | Brem | |
| 6,659,338 B1 | 12/2003 | Dittmann et al. | |
| 6,708,432 B2 | 3/2004 | Haar et al. | |
| 6,968,639 B2 | 11/2005 | Destoumieux | |
| 7,198,629 B2 | 4/2007 | Brem | |
| 7,235,055 B2 | 6/2007 | Pfistershammer | |
| 8,517,957 B2 | 8/2013 | Decaluwe et al. | |
| 8,668,655 B2 * | 3/2014 | Destoumieux ....... A01K 11/003 600/564 | |
| 8,906,310 B2 | 12/2014 | Bonecker | |
| 9,038,293 B2 | 5/2015 | Decaluwe et al. | |
| 9,301,497 B2 | 4/2016 | Decaluwe et al. | |
| 2002/0066418 A1 | 6/2002 | Fearing et al. | |
| 2002/0118595 A1 | 8/2002 | Miller et al. | |
| 2002/0160428 A1 | 10/2002 | Sundrehagen | |
| 2003/0093009 A1 | 5/2003 | Newby et al. | |
| 2004/0103567 A1 | 6/2004 | Destoumieux | |
| 2004/0167429 A1 * | 8/2004 | Roshdieh et al. ............ 600/567 | |
| 2004/0242960 A1 | 12/2004 | Orban, III et al. | |
| 2005/0051109 A1 | 3/2005 | Fantin et al. | |
| 2005/0155440 A1 | 7/2005 | Kanjilal et al. | |
| 2005/0228310 A1 | 10/2005 | Pfistershammer | |
| 2005/0256425 A1 * | 11/2005 | Prusiner ..................... 600/567 | |
| 2006/0021673 A1 | 2/2006 | Rodewald | |
| 2007/0103314 A1 | 5/2007 | Geissler | |
| 2007/0142743 A1 | 6/2007 | Provencher et al. | |
| 2007/0239067 A1 | 10/2007 | Hibner et al. | |
| 2007/0293826 A1 * | 12/2007 | Wall et al. .................... 604/200 | |
| 2008/0044313 A1 | 2/2008 | Caisley | |
| 2008/0064983 A1 * | 3/2008 | Stromberg et al. ........... 600/567 | |
| 2008/0222930 A1 | 9/2008 | Pennington et al. | |
| 2008/0227662 A1 | 9/2008 | Stromberg et al. | |
| 2008/0228105 A1 | 9/2008 | Howell et al. | |
| 2009/0131825 A1 | 5/2009 | Burbank | |
| 2009/0326548 A1 | 12/2009 | Nehls et al. | |
| 2010/0016758 A1 | 1/2010 | Hilpert | |
| 2010/0325926 A1 | 12/2010 | Hilpert et al. | |
| 2011/0295148 A1 * | 12/2011 | Destoumieux ....... A01K 11/003 600/564 | |
| 2012/0010526 A1 | 1/2012 | Hilpert et al. | |
| 2013/0175347 A1 | 7/2013 | Decaluwe et al. | |
| 2013/0195542 A1 | 8/2013 | Decaluwe et al. | |
| 2013/0211287 A1 | 8/2013 | Decaluwe et al. | |
| 2013/0211416 A1 | 8/2013 | Teychene et al. | |
| 2014/0083367 A1 | 3/2014 | Kellerby et al. | |
| 2014/0249449 A1 | 9/2014 | Hilpert et al. | |

FOREIGN PATENT DOCUMENTS

| | | |
|---|---|---|
| EP | 0212885 | 9/2001 |
| EP | 1504722 | 2/2005 |
| EP | 1759638 A1 | 3/2007 |
| EP | 1772104 | 4/2007 |
| EP | 1911347 A1 | 4/2008 |
| EP | 2191715 A1 | 6/2010 |
| FR | 2831389 A1 | 5/2003 |
| FR | 2917574 A1 | 12/2008 |
| FR | 2924899 A1 | 6/2009 |
| FR | 2939281 A1 | 6/2010 |
| FR | 2961088 A1 | 12/2011 |
| FR | 2963203 A1 | 2/2012 |
| FR | 2963536 A1 | 2/2012 |
| FR | 2963722 A1 | 2/2012 |
| FR | 2978328 A1 | 2/2013 |
| FR | 2961087 B1 | 6/2013 |
| FR | 2940011 B1 | 11/2014 |
| GB | 2358061 A | 7/2001 |
| JP | 2006026227 A | 2/2006 |
| WO | 9626675 A1 | 9/1996 |
| WO | 0189388 A1 | 11/2001 |
| WO | 2002039810 A2 | 5/2002 |
| WO | 2002078431 A2 | 10/2002 |
| WO | 2004010773 | 2/2004 |
| WO | 2005110602 A1 | 11/2005 |
| WO | 2006000869 A2 | 1/2006 |
| WO | 2006045162 A2 | 5/2006 |
| WO | 2007087261 A2 | 8/2007 |
| WO | 2007087355 A2 | 8/2007 |
| WO | 2008003693 A1 | 1/2008 |
| WO | 2008043156 A1 | 4/2008 |
| WO | 2008055690 A1 | 5/2008 |
| WO | 2008152980 A1 | 12/2008 |
| WO | 2009074659 A1 | 6/2009 |
| WO | 2009076469 A1 | 6/2009 |
| WO | 2009089215 A1 | 7/2009 |
| WO | 2009149716 A1 | 12/2009 |
| WO | 2010063287 A1 | 6/2010 |
| WO | 2010066475 A1 | 6/2010 |
| WO | 2010070130 A2 | 6/2010 |
| WO | 2011047902 A1 | 4/2011 |
| WO | 2011154233 A1 | 12/2011 |
| WO | 2011154510 A1 | 12/2011 |
| WO | 2012013429 A1 | 2/2012 |
| WO | 2012019911 A1 | 2/2012 |
| WO | 2012019956 A1 | 2/2012 |
| WO | 2013014034 A1 | 1/2013 |

OTHER PUBLICATIONS

Search Report for French Application 1054563, completed Jan. 13, 2011, 2 pgs.
Search Report and Written Opinion for International Application PCT/EP2011/059636, completed Jul. 8, 2011.
French International Search Report for Application 1056600, dated Mar. 2011, 2 pgs.
International Preliminary Report on Patentability for International Application No. PCT/EP2008/067354, dated Aug. 3, 2010, 12 Pgs.
International Preliminary Report on Patentability for International Application No. PCT/EP2009/059981, dated Jun. 14, 2011, 12 Pgs.

(56) References Cited

OTHER PUBLICATIONS

International Preliminary Report on Patentability for International Application No. PCT/EP2009/067591, dated Aug. 2, 2011, 14 Pgs.
International Preliminary Report on Patentability for International Application No. PCT/EP2011/058106, dated Dec. 10, 2012, 7 Pgs.
International Preliminary Report on Patentability for International Application No. PCT/EP2011/059636, dated Dec. 10, 2012, 11 Pgs.
International Preliminary Report on Patentability for International Application No. PCT/EP2011/060558, dated Feb. 5, 2013, 8 Pgs.
International Preliminary Report on Patentability for International Application No. PCT/EP2011/062896, dated Feb. 19, 2013, 5 Pgs.
International Preliminary Report on Patentability for International Application No. PCT/EP2011/063407, dated Feb. 12, 2013, 7 Pgs.
International Preliminary Report on Patentability for International Application No. PCT/EP2012/064018, dated Jan. 28, 2014, 11 Pgs.
International Search Report and Written Opinion for International Application No. PCT/EP2009/067591, Search completed Nov. 25, 2010, dated Dec. 2, 2010, 9 Pgs.
International Search Report and Written Opinion for International Application PCT/EP2009/059981, Search completed Nov. 6, 2009, dated Nov. 13, 2009, 9 pgs.
International Search Report for Application PCT/EP2008/067354, report completed Apr. 21, 2009, dated Apr. 28, 2009, 6 pgs.
International Search Report for International Application No. PCT/EP2011/058106, Search completed Jul. 4, 2011, dated Jul. 13, 2011, 5 pgs.
International Search Report for International Application No. PCT/EP2012/064018, International Filing Date Jul. 17, 2012, Search Completed Oct. 4, 2012, dated Oct. 15, 2012, 3 pgs.
International Search Report for International Application PCT/EP2011/063407, Search completed Oct. 31, 2011, dated Nov. 10, 2011, 5 Pgs.
Preliminary Search Report for Application No. FR 1056349, Completed Mar. 4, 2011, 2 pgs.
Written Opinion for International Application No. PCT/EP2012/064018, International Filing Date Jul. 17, 2012, Search Completed Oct. 4, 2012, dated Oct. 15, 2012, 10 pgs.
Written Opinion for International Application PCT/EP/2008/067354, 10 pgs.
Written Opinion for International Application PCT/EP2011/058106, 11 pgs.
French International Search Report for Application 1056520, dated Apr. 14, 2011, 2 pgs.
International Search Report and Written Opinion for International Application PCT/EP2011/060558 completed Aug. 19, 2011, 9 pgs.
International Search Report and Written Opinion for International Application PCT/EP2011/062896, Report completed Sep. 16, 2001, 7 pgs.
Search Report for French application 1054564, 2 pgs.
Written Opinion for International Application PCT/EP2011/063407, Search completed Oct. 31, 2011, dated Nov. 10, 2011, 6 Pgs.

\* cited by examiner

TOOL FOR COLLECTING A SAMPLE OF ANIMAL TISSUE

1. FIELD OF THE INVENTION

The field of the invention is that of the control and/or identification of animals.

More specifically, the invention pertains to the collection of tissue from an animal, making it possible especially to preserve cells carrying the animal's biological or biochemical characteristics, for example in order to subsequently identify the animal or detect diseases in the animal.

More specifically, the invention pertains to the tool used to make such a collection.

The invention enables tissue samples from cows, sheep, pigs, goats, poultry, fish or more generally any animal species to be collected with or without the simultaneous placing of an identifying tag.

2. PRIOR ART

In order to improve the tracking of livestock, improve productivity (by eliminating diseased animals or by searching for singular genetic characteristics for example) and guarantee the origin of animals intended especially for consumption (for example by detecting disease), it is becoming a frequent practice to make one or more collections of tissue samples from the animals concerned.

Such collecting of samples can be done directly on the animal when placing a tag to identify the animal (at birth for example) or later. Other sample-collecting operations can be done throughout the animal's life span, for example to detect disease or certify the animal's identity, for example by comparing DNA sequences. Once collected, the sample of animal tissue can therefore be stored and/or transmitted to a laboratory for analysis.

Currently used collecting techniques enable a sample of tissue to be taken from the animal when placing an identification tag which may be visual or electronic.

Unfortunately, these sample-taking techniques call for an adaptation of the existing tags, both in structure and in the materials used. These constraints can give rise to problems of behavior of the tags such as poor lasting quality of the tag or premature ageing.

Tissue-collecting techniques implemented independently of the placing of an identification tag are also known.

As illustrated in FIG. 1, these techniques rely for example on the use of a punch forming or comprising a cutting element 10 designed to cut out a sample 11 of animal tissue and collect it in a housing. To this end, the cutting element 10 has a generally circular cutting edge that works by continuous contact or is serrated.

The punch 10, fixed to a first jaw of a tool for collecting, a clamp for example, cuts out the animal's skin and gets at least partially inserted into the microtube 12 fixed to a second jaw of the tool, during the actuation of the tool. The punch 10 classically has a diameter slightly smaller than that of the microtube 12 so as to serve as a plug for the microtube. The housing that receives the sample 11 is therefore open towards the interior of the microtube but closed towards the exterior of the microtube so as to prevent any contamination of the sample.

By means of these collecting techniques, the sample 11 is directly inserted into the microtube 12 thus limiting risks of contamination of the sample.

Unfortunately, one drawback of this technique is that hairs of the animal often remain wedged between the walls of the microtube and the punch serving as a plug, giving rise to a problem of imperviousness of the receptacle. The preservation of the sample is therefore not ensured.

Furthermore, once the punch is inserted into the microtube, it is no longer possible to add any product into the microtube such as a preserving agent or a reagent without having to withdraw or cut out the punch.

Yet another drawback of this technique is that the punch has to be manipulated in order to extract the sample of tissue collected in the housing, and this operation could prove to be difficult and/or complicated and present a risk of inflicting cuts on the user.

There is therefore need for a novel technique for collecting tissue from an animal that does not have all these prior-art drawbacks.

3. SUMMARY OF THE INVENTION

The invention proposes a novel solution that does not have all these drawbacks of the prior art in the form of a tool for collecting a sample of animal tissue, intended for cooperating with collecting means comprising at least one cutting element designed to cut out the sample and one pusher element that is mobile relatively to the cutting element, design to push the sample into storage means after cutting.

According to the invention, such a tool comprises:
  means for driving the cutting element, enabling the cutting element to be moved along an axis of translation in the direction of the tissue,
  means for driving the pusher element making it possible to move the pusher element along the axis of translation in the direction of the tissue until the pusher element is at least partially inserted into the storage means,
  means for the reversible coupling of the means for driving the cutting element and the means for driving the pusher element, these coupling means being mobile between two positions:
    a coupling position enabling the movements of the cutting and pusher elements to be linked together, and
    a decoupling position enabling the movements of the cutting and pusher elements to be dissociated.

The invention thus proposes a novel tool for collecting animal tissue, enabling the simultaneous actuation of the means for driving the cutting element and the means for driving the pusher element in a first stage and then only the means for driving the pusher element in a second stage, through only one action on the tool.

In other words, the operations for cutting out tissue, extracting tissue and closing the tube are done in only one action, that is only one movement for the user (actuation of a lever, triggering of a trigger etc).

The proposed tool can be seen as a dual-pin (or dual-rod) mechanism, with one primary pin (or rod) transmitting the motion of translation to the cutting element in order to cut out the tissue sample and one secondary pin (or rod) transmitting the motion of translation to the pusher element along a same direction to extract the cut-out tissue, these two pins being linked together until the tissue is cut out, and being then disconnected. The path of the cutting element and of the pusher element through the animal tissue (the ear for example) is therefore rectilinear.

The invention thus enables an optimized collecting, particularly simple and swift for the user, who does not himself have to perform several actions for perforating the animal tissue, pushing the sample into the storage means, closing the storage means etc, all these operations being done through a single action on the tool (for example a manual, electrical, pneumatic or other action on the grips of the tool).

Furthermore, a potential contamination of the sample is averted since the user does not have to act directly on the sample. Besides, since the sample is cut out by the cutting element and then automatically pushed into storage means by the pusher element, no portion of the tool or no external element is in direct contact with the collected tissue.

According to one particular characteristic of the invention, the tool for collecting comprises at least one hinged grip forming a lever that is mobile on a predetermined course comprising a first portion and a second portion.

A lever of this kind comprises means of action on the coupling means enabling passage from the coupling position on the first portion to the decoupling position on the second portion.

Thus, when the user exerts pressure on the lever, it passes:
from an initial position to an intermediate position corresponding to a first portion of the course of the lever during which the means for driving the cutting element and the means for driving the pusher element are coupled; then
from the intermediate position to a final position, corresponding to a second portion of the travel of the lever, during which the means for driving the cutting element and the means for driving the pusher element are decoupled.

According to a first embodiment, the coupling means implement at least one mobile coupling element designed to cooperate with a housing made for this purpose in the means for driving the cutting element, the coupling element or elements being held in the housing in the coupling position and being released in the decoupling position.

It can be noted that several coupling elements can be planned (for example one, two or three such elements).

This first embodiment makes it possible to do away with the use of prestressed springs designed to get compressed from a certain force onwards.

Thus, in the decoupling position, it is not necessary to cumulate the cutting forces and the forces used to close the storage means.

Furthermore, according to this first embodiment, the coupling means delink the means for driving the cutting element from the means for driving the pusher element according to the course of the lever and not the different forces that come into play: resistive force to pass through the animal tissue (which differ according to the area in which the collecting is made (owing to a variation in the thickness of the tissue in particular) depending on the breed or category of the animal, the orientation of the tool relatively to the tissue to be collected, etc), a force for closing the storage means, a force exerted on the lever etc. This enables improved repeatability of the operation since the course of the lever is always identical while the force exerted on the lever can be variable.

In particular, according to this first embodiment, the means for driving the pusher element comprise at least one groove and the housing faces the groove in the coupling position.

In this way, in the coupling position, the groove also receives the coupling element provided in the corresponding housing.

For example, the coupling element is a ball, a cylinder etc.

According to one particular aspect, the housing is a through aperture and the ball is held in the housing by means of a sliding part shaped to define holding means holding the ball in the groove in the coupling position and releasing means releasing the ball from the groove in the decoupling position.

For example, the sliding part has a shape generated by revolution about the axis of translation defining a sleeve comprising at least two sections of distinct diameters, the holding means corresponding to the section of smaller diameter and the releasing means to the section of greater diameter.

The sliding part can be connected to the means for driving the pusher element by a spring, called a slide spring, the slide spring tending to move the sliding part away from the means for driving the pusher element. For example, the slide spring is in an idle state in the coupling position and in a compressed state in the decoupling position.

According to a second embodiment, the coupling means implement a system known as a "stripping" system.

More specifically, the coupling means implement a coupling spring positioned between the means for driving the cutting element and the means for driving the pusher element, said coupling spring being prestressed so as to necessitate the application of a force greater than the force needed to cut out the sample in order to get compressed.

The prestressed coupling spring thus fulfils the function of coupling the driving means of the pusher element and the means for driving the cutting element so long as the tissue is not cut out, and then enables the shifting of the pusher element independently of the cutting element when the tissue cutting-out force is exceeded.

The solution according to this second embodiment is particularly simple to implement since it calls solely for the adding of a prestressed spring.

According to a third embodiment, the coupling means implement a clip-on system with at least one at least partially deformable element.

For example, such an element comprises a plurality of tongues or leaf springs extending substantially in parallel to the axis of translation, the tongues each having at least one boss capable of cooperating with a complementary housing planned in the means for driving the cutting element in the coupling position.

According to this third embodiment, the means for driving the cutting element therefore have a specific shape enabling them to get coupled reversibly with this at least partially deformable element.

Again, this third embodiment makes it possible to do away with the use of prestressed springs, which are to get compressed upon and beyond the application of a certain force. In the decoupling position, it is therefore not necessary to cumulate the cutting-out forces and the forces for closing the storage means.

Furthermore, as in the case of the first embodiment, the coupling means delink the means for driving the cutting element from the means for driving the pusher element depending on the course of the lever, and not on the different forces that come into play according to this third embodiment, thus enabling greater repeatability of the operation.

According to another characteristic of the invention, the tool for collecting comprises means for locking the storage means on to one arm of the tool.

For example, these locking means are of a locking ring, translating element or other such type.

They enable the storage means, for example a sampling tube, to be held securely during the collecting operation. Once the collecting is done, the user can simply unlock these means to have access to the tube containing the sample. In this way, the user does not have to have to handle the sample directly.

According to another characteristic, the tool for collecting comprises means for ejecting the cutting element.

For example, after the tissues are cut out, the used cutting element is brought into the initial position and ejects the tool by a deliberate action on the part of the user, such as an action of the lever in a reverse sense for example, without direct contact with the user, in order to throw the cutting element into an appropriate area (a garbage can, a retrieval bin, etc).

In this way, the user does not have to handle the soiled cutting element thus preventing the risk of injury and contamination.

The tool for collecting is therefore designed so that at no time is the user in direct contact with the soiled cutting element and the collected sample.

According to another embodiment of the tool for collecting, the means for driving the cutting element comprise a main piston and the means for driving the pusher element comprise a secondary piston, the secondary piston being shifted by inertia into the decoupling position.

According to this embodiment, a simple push by the user on a button or a trigger activates the simultaneous shifting of the main and secondary pistons in a first stage, and then only that of the secondary piston in a second stage, by inertia, after a sudden stopping of the motion of the main piston.

In particular, according to this embodiment, the coupling means include a locking pin cooperating with a slot provided in the main piston, the locking pin being blocked in the decoupling position.

Thus, the sudden stopping of the motion of the main piston can be prompted by the blocking of the locking pin, making the coupling means pass from the coupled position to the decoupled position.

According to one particular aspect of the invention, the tool for collecting comprises means for the automatic withdrawal of the cutting element.

Such means enable the animal's ear to be swiftly released and prevent the risks that the user or the animal might be cut with a soiled cutting element, in protecting the cutting edge of the cutting element.

4. LIST OF FIGURES

Other features and advantages of the invention shall appear more clearly from the following description of a particular embodiment, given by way of a simple, illustratory and non-exhaustive example and from the appended drawings, of which:

FIG. 1 illustrates a device for collecting a tissue sample according to the prior art;

FIGS. 2 and 3 respectively present a view in section of the means for collecting and the means for storing that can be implemented by a tool for collecting according to one embodiment of the invention;

FIG. 4 illustrates a tool for collecting according to one embodiment of the invention in an initial position;

FIGS. 5A and 5B provide a more precise illustration of the different elements of the tool for collecting according to FIG. 4 during collection;

FIGS. 6 and 7 show an example of a mechanism for ejecting the cutting element of the tool for collecting of FIG. 4;

FIGS. 8A and 8B respectively illustrate the collecting tool of FIG. 4 and the storage means after the collecting operation;

FIGS. 9A and 9B propose a first example of an embodiment of the coupling means according to the invention;

FIGS. 13A to 15 present different techniques enabling an automatic withdrawal of the cutting element after the cutting out of the tissues.

5. DESCRIPTION OF ONE EMBODIMENT OF THE INVENTION

5.1 General Principle

The general principle of the invention relies on a specific collecting tool working in two stages, enabling the use of collecting means comprising a cutting element and a pusher element to collect a sample of animal tissue as described for example in the patent application filed under number FR-08 58453.

More specifically, a collecting tool of this kind enables the simultaneous shifting of the cutting element and the pusher element in a first stage and then the shifting of the pusher element alone in a second stage.

The tool according to the invention thus comprises means for driving the cutting element and means for driving the pusher element, enabling the cutting element and the pusher element to be moved towards the tissue to be collected, and means for the reversible coupling of the means for driving the cutting element and the means for driving the pusher element.

These coupling means enable two positions to be defined:
a coupling position enabling the linking of the motions of the cutting element and pusher element and therefore enabling these two elements to be shifted simultaneously, and
a decoupling position enabling the motions of the cutting element and pusher element to be dissociated and therefore enabling the pusher element to be shifted separately.

5.2 Description of One Particular Embodiment

Here below, we describe a particular embodiment in which the tool for collecting according to the invention is used to make a collection by using the means for collecting and storing as described in the French patent application FR-08 58453.

A) Means for Collecting

Here below, we recall the main characteristics of the means for collecting described in the French patent application FR-08 58453.

Figure 1:
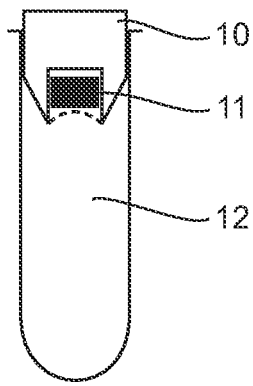
Figure 2:
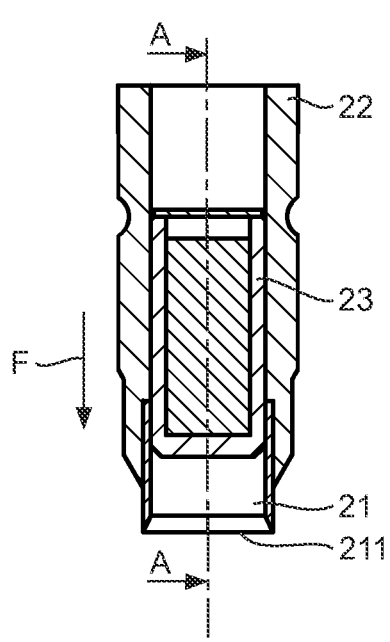

As illustrated in FIG. 2, these means for collecting comprise firstly a cutting element 21 and secondly a pusher element 23. The cutting element 21 can especially be fixedly joined to a support 22. This support 22 which can be made out of plastic, is meant to be detachably mounted on the end of a rod fixedly joined to one of the arms of a tool for collecting. It takes the form of a surface generated by revolution having the same axis as the cutting element 21 and the pusher element 23. It comprises especially a flange 221 on which it is possible to fix the rod to drive the cutting element.

According to one variant, the cutting element 21 and the support 22 are formed as an integral piece, for example made of plastic or metal. The cutting element 21 and the support 22 are herein deemed to form a single piece, which is a "monoblock" unit.

The cutting element 21 is deemed for example to have a shape generated by cylindrical revolution. The cutting edge 211 then has a circular shape.

The cylinder forming the cutting element 21 is open at both ends in order to let through the pusher element 23 so that the latter can push the sample out of the cutting element 21 and accompany it into the storage means along the direction illustrated by the arrow F.

According to the exemplary embodiment illustrated, the pusher element 23 also has a cylindrical shape generated by revolution. However, the diameter of the pusher element 23 must be smaller than that of the cutting element 21 so that the pusher element 23 can slide into the cylinder formed by the cutting element 21.

The pusher element 23 is mobile in translation along the axis A-A within the cutting element 21 along the direction illustrated by the arrow F.

B) Storage Means

We also recall the main characteristics of the storage means described in the French patent application FR-08 58453.

Figure 3:
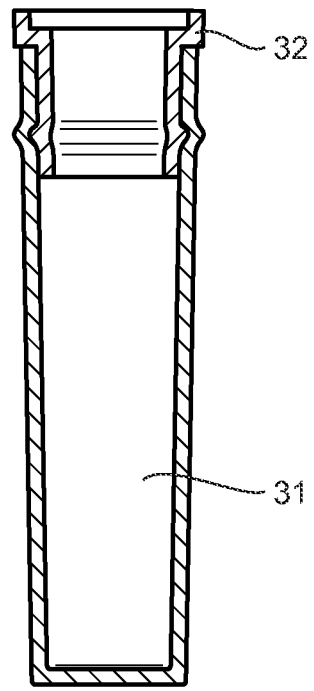

As illustrated in FIG. 3, these storage means comprise firstly a sampling tube 31 comprising at least one aperture and secondly a tube top piece 32 fixedly joined to the inlet of the sampling tube, for example by being clipped on or by being fitted in. It can be made out of a flexible material, for example rubber, to facilitate its insertion into the neck of the tube.

More specifically, the tube top piece 32 takes the form of a hood perforated with a central aperture having a diameter sufficient to enable the insertion of at least one portion of the pusher element 23. The use of a flexible material for this hood also facilitates the insertion of the pusher element 23 into the tube 31. The pusher element 23 then closes the tube 31 imperviously or almost imperviously.

The tube top piece 32 also has a flange resting on the rim of the sample tube 31, defining a stop surface (or block) on which the cutting edge of the cutting element 21 can take support during the collecting operation in order to cut out the tissue sample more easily.

C) Tool for Collecting

Here below, we describe several examples of the tool for collecting, sometimes also called an applicator or pliers, which can be used to collect a tissue sample according to the invention.

i) General Operation

Figure 4:
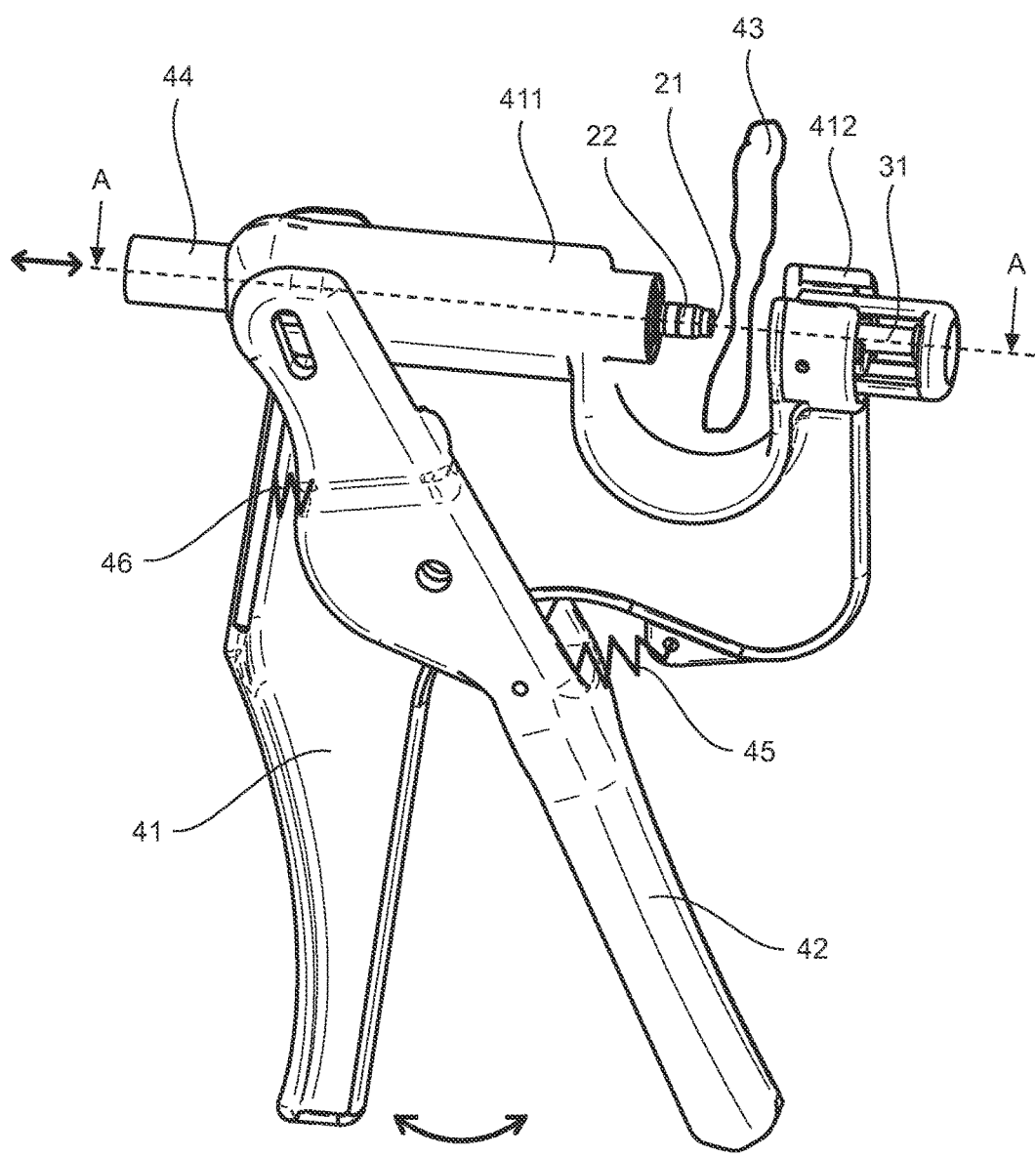

As illustrated in FIG. 4, a tool of this kind generally has a fixed part also called a body 41 defining especially a first grip and a hinged part also called a lever 42 defining a second grip.

The body 41 of the tool also defines two arms between which the tissue to be collected, for example the animal's ear 43, is positioned. Thus, the first arm 411 is designed to cooperate with collecting means as illustrated in FIG. 2 for example and the second arm 412 is designed to cooperate with storage means as illustrated in FIG. 3 for example.

More specifically, the second arm 412 comprises means for locking the sampling tube such as a locking ring for example.

The first arm 411 for its part comprises means 44 for driving the collecting means, enabling the cutting element 21 (and/or its support 22) and the pusher element 23 to be moved in translation towards the tissue to be collected, along the translation axis A-A. These driving means are activated when the user of the tool exerts a force on the lever 42.

Thus, the lever 42, which can be actuated by hand for example, acts on the driving means 44 so as to guide the collecting means in a motion of translation so that they penetrate the animal's flesh and force the collected sample into the storage means. The tool can also be actuated by means of electrical, pneumatic or other power. The collecting and storage means are therefore configured to cooperate with a tool of this kind.

More specifically, the driving means 44 include means for driving the cutting element 21 (and/or its support 22), means for driving the pusher element 23 and means for reversibly coupling these driving means. Thus, in a first stage, corresponding to a first portion of the course of the lever 42 between an initial position and an intermediate position, the driving means of the cutting element 21 and the means for driving the pusher element 23 are coupled in a coupling position enabling the movements of the cutting element and pusher element to be linked. In a second stage, corresponding to a second portion of the course of the lever 42 between the intermediate position and a final position, the means for driving the cutting element 21 and the means for driving the pusher element 23 are decoupled in a decoupling position enabling the motions of the cutting and pusher elements to be dissociated.

FIG. 4 illustrates the initial state of the applicator when the collecting and storage means are mounted on the tool which is ready for use.

Figure 5A:
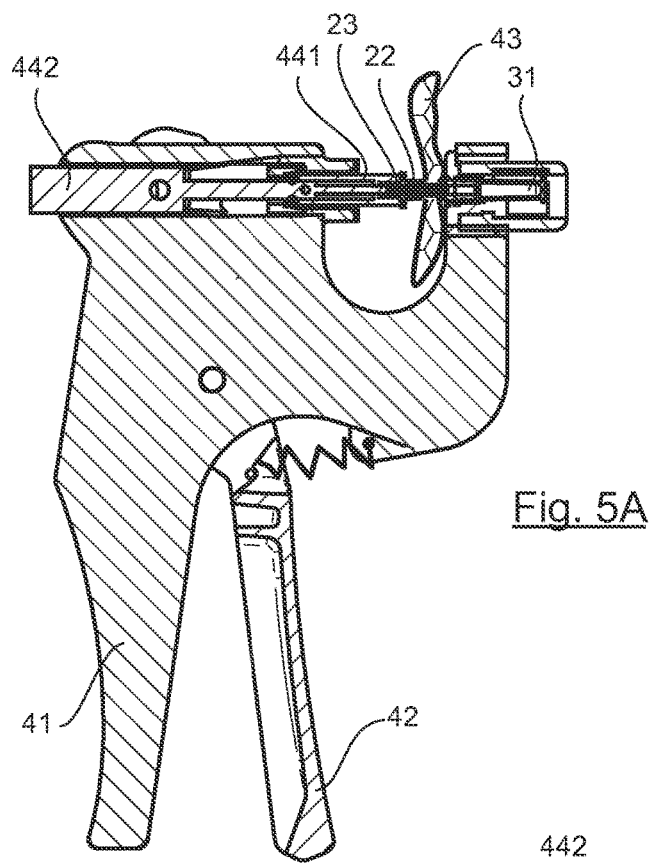
Figure 5B:
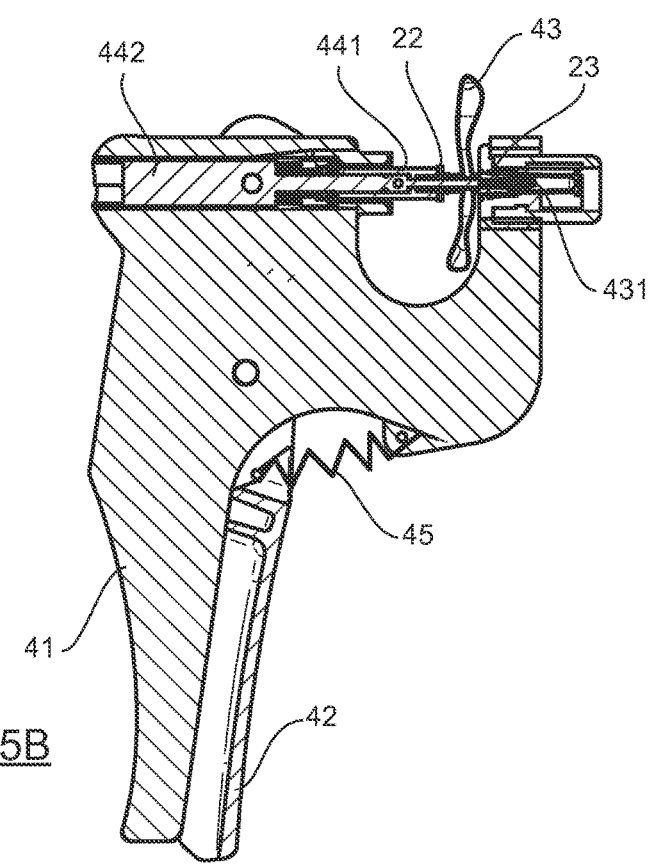

FIGS. 5A and 5B provide a more precise illustration of the different elements of the tool for collecting during collection and especially the two positions, namely the coupling and decoupling positions. The cutting element 21 is deemed for example to be guided in translation by the driving means 441 and the pusher element 23 is deemed for example to be guided in translation by driving means 442 pushing the pusher element 23 through the cutting element 21.

As illustrated in FIG. 5A, the driving means 441 of the cutting element and the driving means 442 of the pusher element are linked in a coupling position in a first stage corresponding to the first position of the course of the lever 42. The action on the lever 42 between its initial position and its intermediate position corresponding to the first portion of its course then give rise to the simultaneous translation of the cutting element 21 (or of its support 22) and the pusher element 23 along the same axis of translation.

This translation enables the cutting element to perforate the ear 43 in a rectilinear path to cut out a sample of tissue until it abuts the flange of the tube top piece of the sampling tube 31.

In a second stage, corresponding to a second portion of the course of the lever 42, as illustrated in FIG. 5B, the driving means 441 of the cutting element and the driving means 442 of the pusher element are no longer linked. Thus, in this decoupling position, the continuance of the action on the lever 42 on this second portion gives rise to a translation of the pusher element 23 alone. The pusher element 23 is then guided in translation through the cutting element 21 (blocked in an abutting position against the flange of the tube top piece) and pushes the cut-out sample 431 up to the tube 31. The pusher element 23 ends its course in getting fitted into the tube top piece and thus hermetically or almost hermetically blocks the tube 31.

In other words, the action of the pusher element starts after the cutting element has cut out tissue against an "anvil" (the flange of the tube top piece of the sampling tube 31) thus ensuring a clean and repeatable cut of the first skin, the cartilage, and the second skin.

With the sample-collecting having being done in a sure way, the user can then release the lever 42. A return spring 45 or any other means can then bring the lever into its initial position as well as bring the driving means 441 of the cutting element and the driving means 442 of the pusher element back to their initial position, i.e. to their coupling position.

The cutting element can thus be brought to the initial position. In this way, the cutting element remains neither in the storage means nor in the animal and can take any form particularly well suited to cutting out animal tissue and especially the form of an extremely cutting edge.

Figure 6:
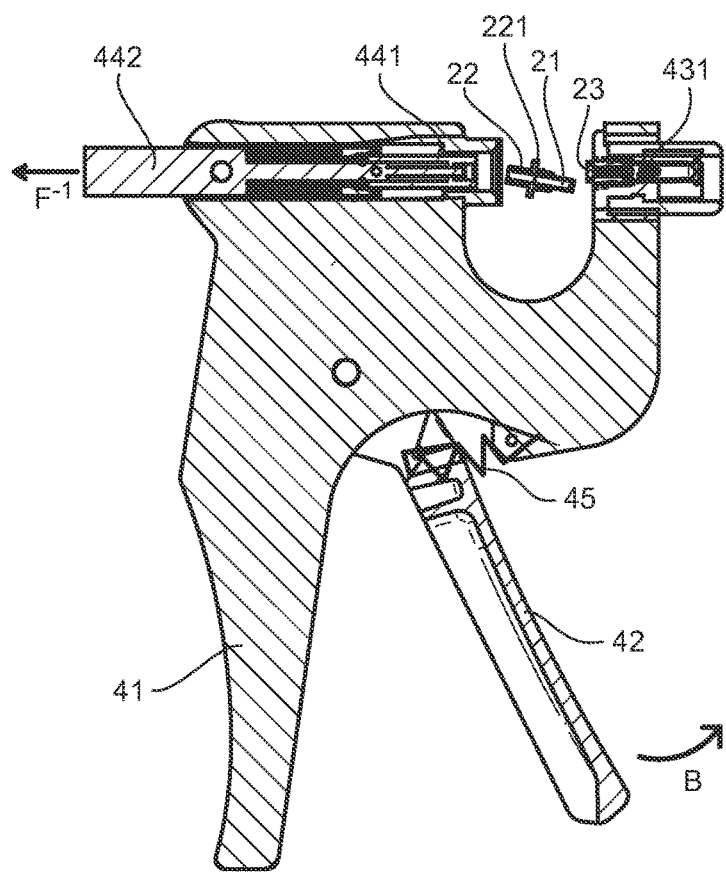

According to one particular aspect of the invention illustrated in FIG. 6, the collecting tool provides for means to eject the cutting element 21 after use. For example, the user can apply a reverse motion of rotation (or translation) to the lever 42, tending to move the first grip 41 away instead of approaching it (arrow B). This movement of reverse rotation (or translation) gives rise to a translation of the means 441 for driving the cutting element and the means 442 for driving the pusher element in a direction $F^{-1}$, opposite to the collecting direction F. The means 441 for driving the cutting element then drive the cutting element 21 in the direction $F^{-1}$ until the flange 221 of the support 22 of the cutting element abuts the means planned for this purpose on the body of the tool. This support 22 and the cutting element 21 are then disconnected from the driving means 441 and ejected from the tool for collecting without the user needing to touch the soiled cutting element.

The user can thus eject the soiled cutting element, when he wishes, into an appropriate place, without having to touch this element, thus preventing risks of cutting or contamination.

Prior to the ejection, the user can of course position a protective element on the cutting element 21.

Figure 7:
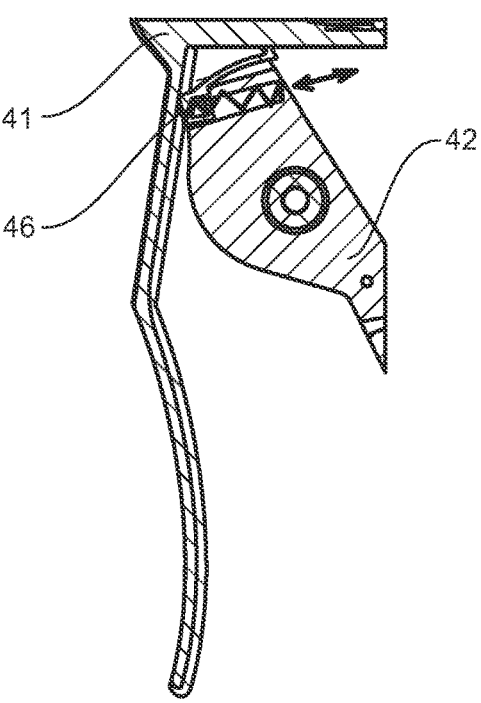

According to this aspect, the stopping of the lever in the initial position (or idle position, is considered to be elastic. It can be made by a damper system or a spring 46 as illustrated in FIG. 7 bringing the lever 42 and the entire mechanism into the initial position. The movement of the lever 42 relatively to the body 41 in the sense opposite to the collecting sense is therefore permitted.

Figure 8A:
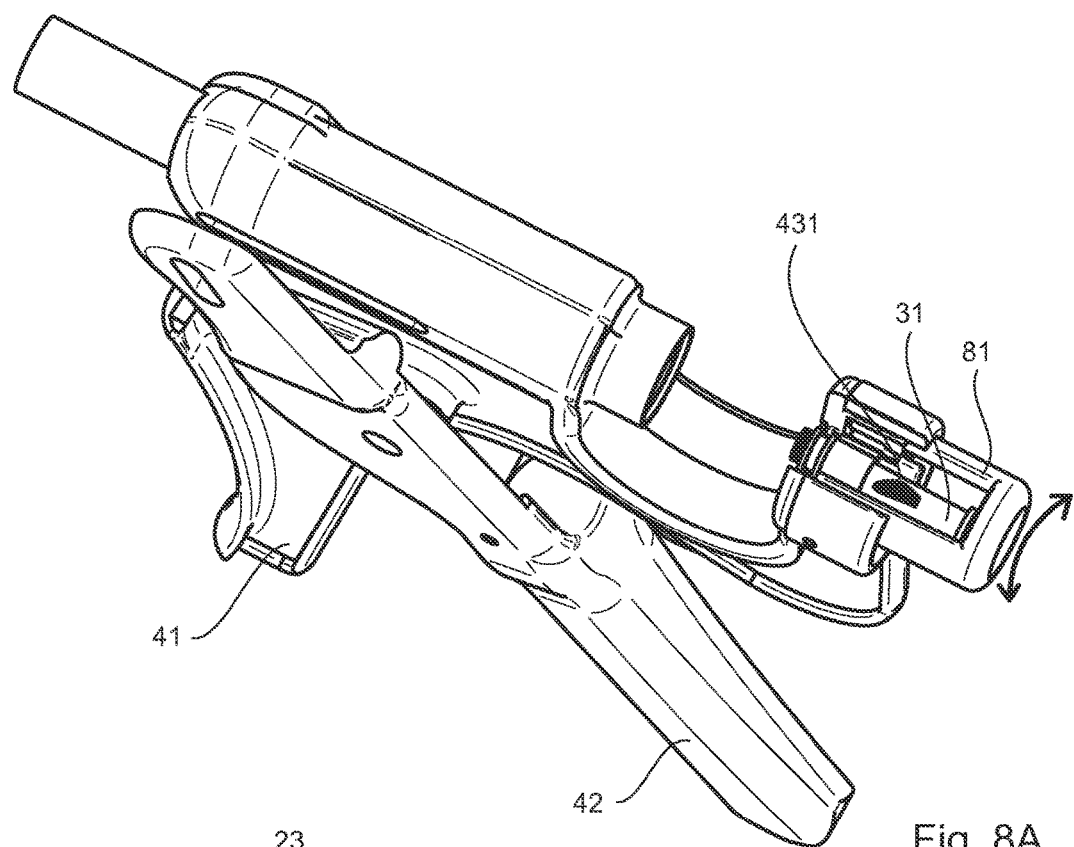
Figure 8B:
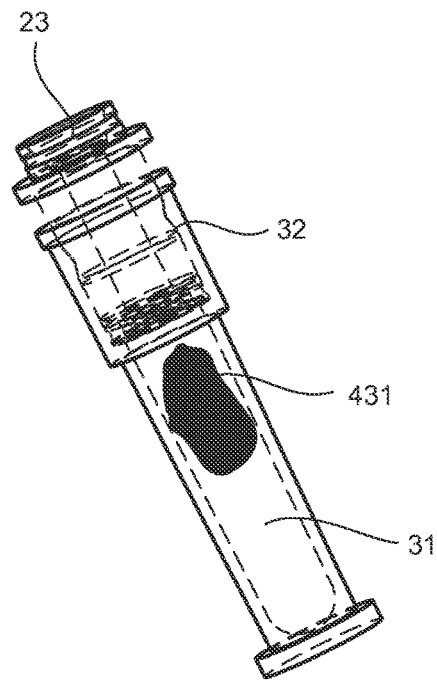

Finally, the user can unlock the locking means 81 from the tube 31, for example by turning a locking ring, or by translating a locking element, in order to retrieve the sample 431 conditioned in the tube 31 as illustrated in FIG. 8A. As illustrated in FIG. 8B, the sample 431 is then ready to be transmitted to a laboratory in its sampling tube 31 plugged by the pusher element 23.

ii) First Example of an Embodiment of the Coupling Means

Here below, we describe a first example of an embodiment of the coupling means enabling the passage from a coupling position of the means 441 for driving the cutting element and of the driving means 442 to the decoupling position.

According to this first example, the coupling means implement at least one mobile coupling element capable of cooperating with a housing made to this effect in the means 441 for driving the cutting element. These coupling means (balls, cylinders or the like) are kept in the housing in the coupling position and released in the decoupling position.

Figure 9A:
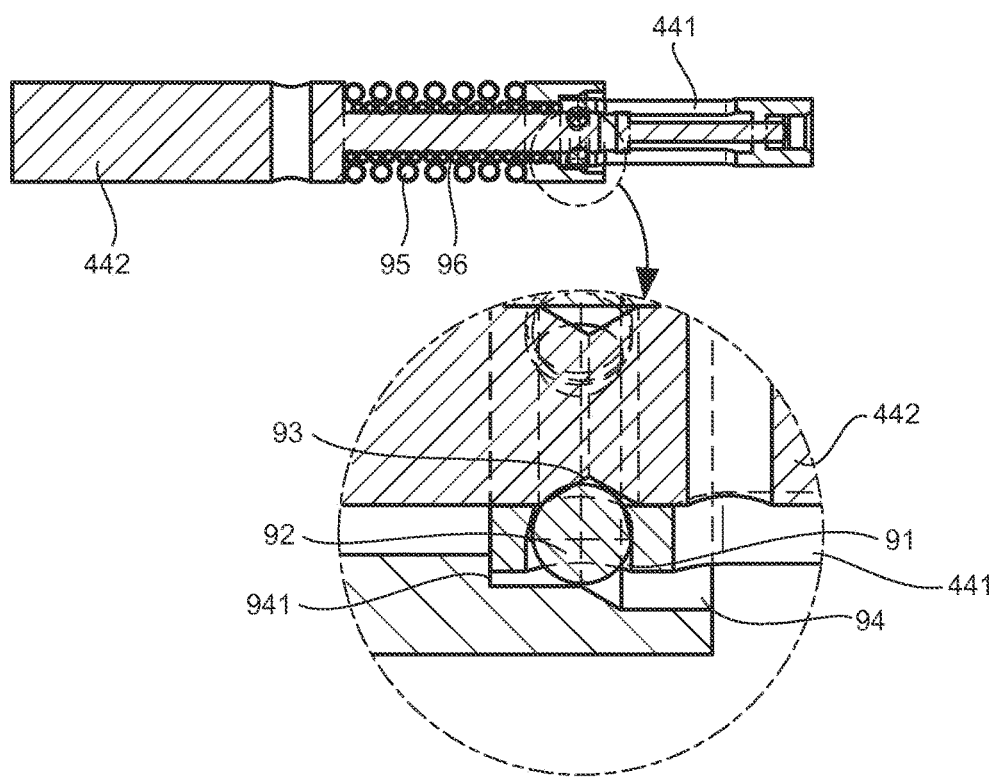
Figure 9B:
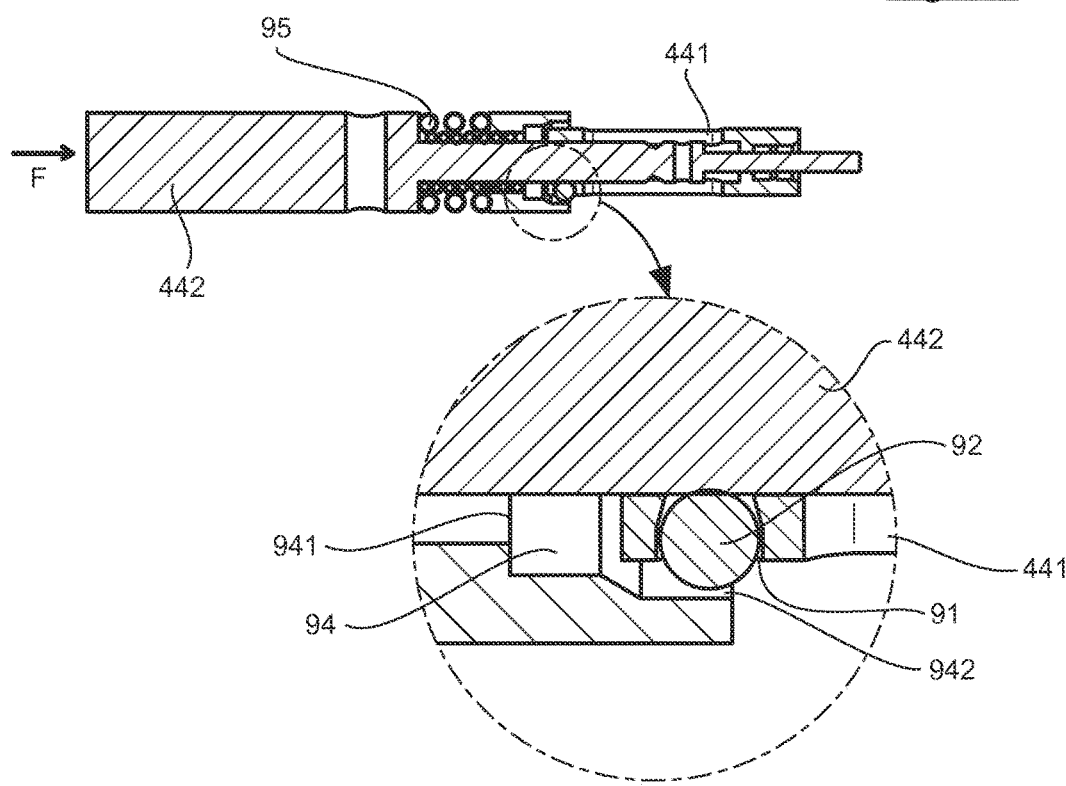

More specifically, FIGS. 9A and 9B illustrate the means 441 and 442 for driving the cutting element and the pusher element corresponding to the positions illustrated respectively in FIGS. 5A and 5B.

According to this first example, the means 441 for driving the cutting element are deemed to comprise one or more housings 91 each receiving a ball 92. The means 442 for driving the pusher element for their part comprise at least one groove 93 such that each housing 91 faces the groove 93 in the coupling position.

In the coupling position illustrated in FIG. 9A, the housing 91 is a through aperture (hole) and the ball 92 is held in the housing 91 by means of a sliding part 94. In the decoupling position illustrated in FIG. 9B, the ball 92 is no longer held by means of the sliding part 94.

For example, a sliding part 94 of this kind has a shape generated by revolution about the axis of translation defining a sleeve comprising at least two sections of distinct diameters. The section 941 with the smallest diameter enables the ball 92 to be held in the groove 93 in the coupling position. The section 942 with the greater diameter enables the ball 92 to be released from the groove 93 in the decoupling position.

The sliding part 94 is connected to the means 442 for driving the pusher element by a spring, called a slide spring 95, proposed according to this example in a state of rest in the coupling position and in a state of compression in the decoupling position.

More specifically, during the collecting, the means 441 for driving the cutting element and the means 442 for driving the pusher element are coupled in a first stage as illustrated in FIG. 9A, thus causing a simultaneous translation of a cutting element and the pusher element.

The cutting element then perforates the animal's ear to cut out a sample of tissue. Just before the cutting element abuts the flange of the tube top piece of the sampling tube, the sliding part 94 is also in an abutment against a stop element (such as a shoulder) provided for this purpose on the body of the tool, at its section 942 with a greater diameter. Since the user continues his action on the lever 42 while the sliding part 94 is in an abutment, the means 442 for driving the pusher element continue to push the pusher element 23 and guide the ball or balls 92 which were hitherto maintained by the section 941 with the smallest diameter of the sliding part 94 towards the section 942 with the greatest diameter. The balls 92 are then released and the means 441 for driving the cutting element and the means 442 for driving the pusher element get decoupled, as illustrated in FIG. 9B, and the pusher element can continue its motion independently of the cutting element.

When the balls are released, the cutting element abuts the flange of the tube top piece of the sampling tube.

It can be noted that the primary spring 96 provided between the means 441 for driving the cutting element and the means 442 for driving the pusher element make it possible to keep the cutting element under pressure against the flange of the tube top piece of the sampling tube, especially when the slide spring 95 gets compressed.

iii) Second Example of an Embodiment of the Coupling Means

Here below, we describe a second example of an embodiment of the coupling means implementing a "stripper" type system.

Figure 10:
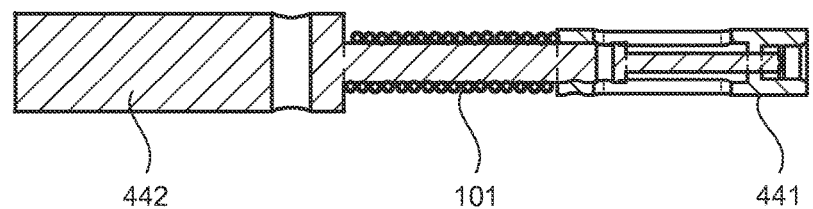
FIG. 10 shows a second example of an embodiment of the coupling means according to the invention.

According to this example, illustrated in FIG. 10, there is provided a coupling spring 101, positioned between the means 441 for driving the cutting element and the means 442 for driving the pusher element.

More specifically, a coupling spring such as this is prestressed and designed to get compressed when a force is applied to it greater than the force needed for the cutting element to cut the sample. It is thus ensured that the movements of the cutting element 21 and the pusher element 23 are identical (means 441 for driving the cutting element and means 442 for driving the pusher element in a coupling position) so long as the cutting element has not perforated the animal tissue.

Indeed, so long as the cutting element does not abut the flange of the tube top piece of the sampling tube, the coupling spring 101 does not get compressed because the force exerted on the cutting element is sufficient to perforate the animal tissue but not sufficient to compress the coupling spring 101.

Once the cutting element is abutting the flange of the tube top piece of the sampling tube, the coupling spring 101 gets compressed if the user continues his action on the lever 42, the force exerted on the cutting element being then greater than that needed to perforate the animal tissue.

For example, if the force needed for the cutting element to cut the sample is deemed to be of the order of 60 Newton, the coupling spring 101 can be prestressed at a force of about 80 to 100 N.

iv) Third Example of an Embodiment of the Coupling Means

Here below, we describe a third example of an embodiment of the coupling means implementing a clip-on system with at least one at least partially deformable element.

Figure 11A:
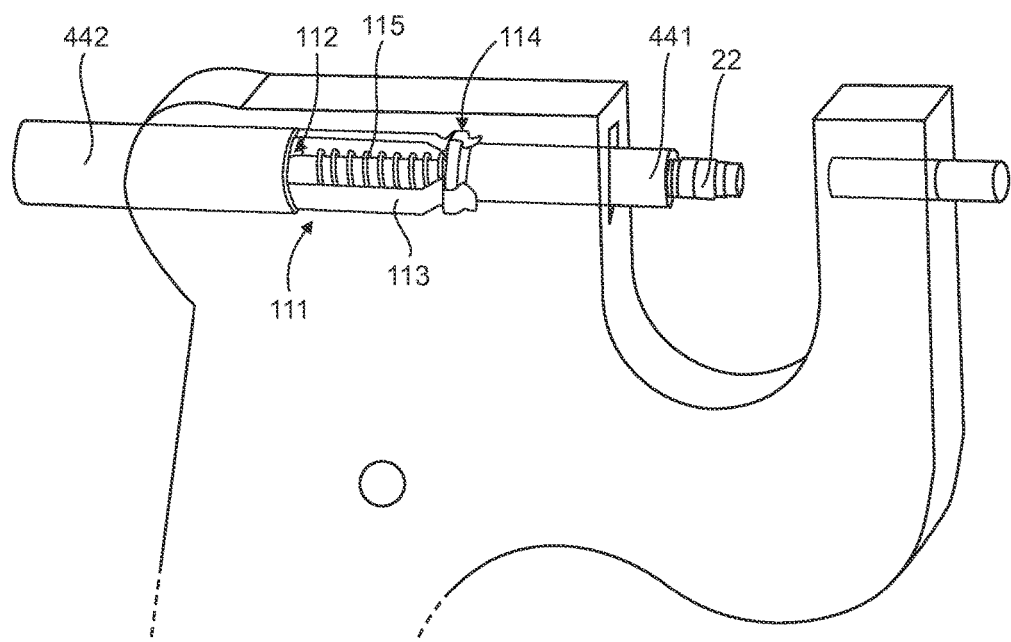
FIGS. 11A and 11B illustrate a third example of an embodiment of the coupling means according to the invention.
Figure 11B:
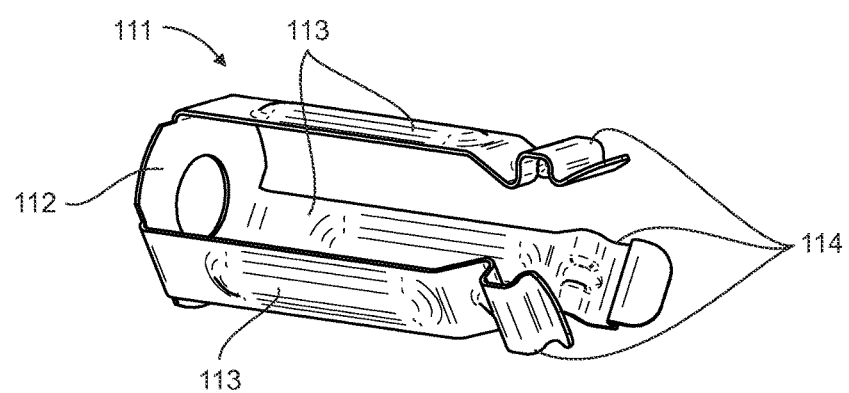

As illustrated in FIGS. 11A and 11B, the at least partially deformable element 111 comprises for example a base 112 designed to take support on the means 442 for driving the pusher element, taking for example the form of a rod. A plurality of tongues, for example three tongues 113, extend from this base 112, substantially in parallel to the axis of translation of the cutting and pusher elements.

Each tongue 113 comprises a boss or a projection 114 capable of cooperating with a matching housing provided in the means 441 for driving the cutting element in the coupling position.

More specifically, the tongues 113 form leaf springs used to hold the means 441 for driving the cutting element in the coupling position.

During the collecting operation, the means 441 for driving the cutting element and the means 442 for driving the pusher element are coupled in a first stage, by means of the partially deformable element 111, as illustrated in FIG. 11A, and this causes the simultaneous translation of the cutting element and the pusher element.

While the cutting element perforates the animal's ear and abuts the flange of the tube top piece of the sampling tube, the means 442 for driving the pusher element continue to push the pusher element 23 and the partially deformable element 111. The user continuing his action on the lever 42, the tongues or leaf springs 113 then spread apart, unclipping the bosses 114 from the complementary housings provided in the means 441 for driving the cutting element, thus releasing the means 441 for driving the cutting element. The means 441 for driving the cutting element and the means 442 for driving the pusher element are then in the decoupling position.

According to one variant, specific deforming means can be planned on the body of the tool to deform the tongues 113 when the free end of these tongues abuts these deforming means.

It can be noted that the primary spring 115, provided between the means 441 for driving the cutting element and the means 442 for driving the pusher element enable pressure to be kept on the cutting element against the flange of the tube top piece of the sampling tube especially when the tongues or leaf springs 113 get deformed.

v) Another Embodiment

Here below, referring to FIGS. 12A to 12H, we present another exemplary embodiment of the invention known as an "inertia-based" embodiment.

In this example, the means for driving the cutting element take the form of a main "piston" 121 and the means for driving the pusher element take the form of a secondary "piston" 122. The main and secondary pistons can slide in the body of the applicator, for example in a first arm, in a movement of translation. The secondary piston can slide within the main piston, also in a movement of translation.

The coupling means comprise especially a "locking pin" 123 held in position in the body of the applicator, cooperating with a slot 1231 provided in the main piston 121. A notch 1232 for releasing the locking pin is also provided at one of the ends of the slot 1231. When the main piston slides in the body of the applicator, the position of the locking pin 123 in the slot 1231 is modified. This corresponds to the coupling position of the main and secondary pistons. In particular, when the locking pin 123 is facing the notch 1232, it is blocked in position, thus releasing the motion of the secondary piston. This corresponds to the decoupling position of the main and secondary pistons.

Figure 12A:
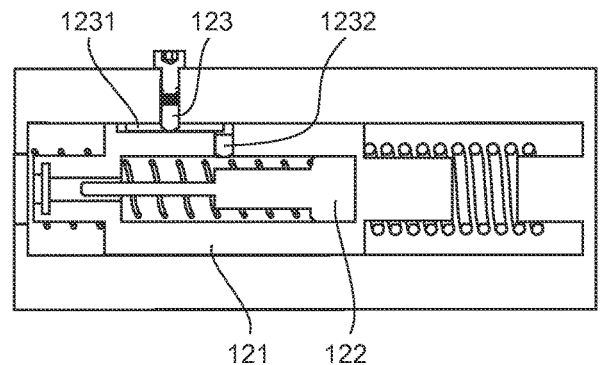
FIGS. 12A to 12H illustrate another example of implementation of the invention.

FIG. 12A provides a more precise illustration of the position of the main piston 121 and secondary piston 122 at rest.

Figure 12B:
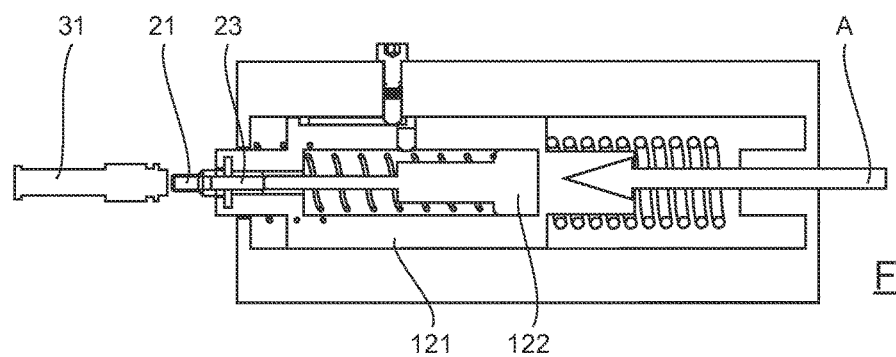

Prior to the collecting operation, the collecting and storage means are mounted on the piston-based system. To this end, as illustrated in FIG. 12B, the user can move the main piston forward along the direction of the arrow A, and therefore the secondary piston, the motion of which is linked to the main piston through the coupling means in coupling position. The collecting means comprise the cutting element 21 (possibly fixedly joined to a support) and the pusher element 23 can then be mounted on the main piston 121. The storage means 31 can be mounted on a second arm of the applicator. It can be noted that the collecting and storage means can be held together by means of a linking piece. This assembly can be fixed to one of the arms of the applicator, for example at the storage means, by a clamp assembly, a locking ring etc. An action by the user on the applicator enables the collecting means to be fixedly joined to the other arm by a clip-on or clamping effect. The linking piece can for example remain on the collecting means in order to protect the cutting element prior to the collection.

Figure 12C:
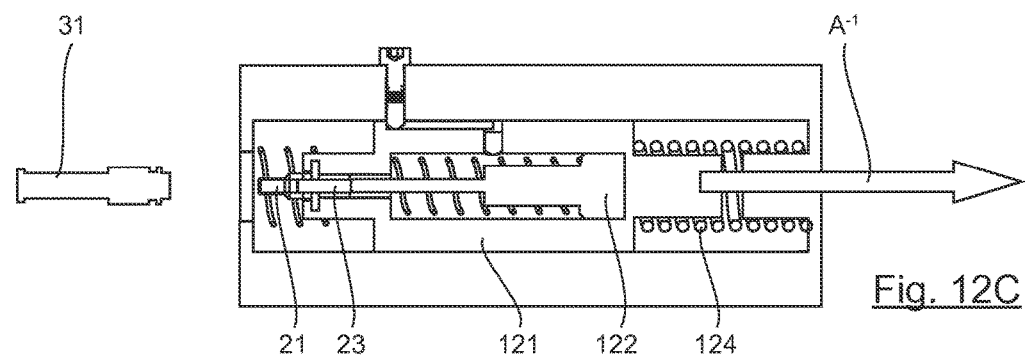

When the user is ready to carry out the collecting operation, he can withdraw or eject the linking piece and "prime" the applicator by bringing the piston-based system along a direction opposite the arrow A as illustrated in FIG. 12C. This operation can be done with a mechanism that increases the force so as to compress a spring 124 linked to the main piston 121 until a locking position is reached. Such a mechanism takes for example the form of a nut with an adapted thread, a lever system, a pump, a rack system, a jack type electrical mechanism, a micromotor etc. The compression of the spring 124 makes it possible to collect energy. During this step, since the coupling means are in a coupling position, the motions of the main and secondary pistons are always linked.

According to one variant not shown, the priming operation can be done by connecting the tool to an external energy source (compressed air in a cartridge or in a network for example).

Figure 12D:
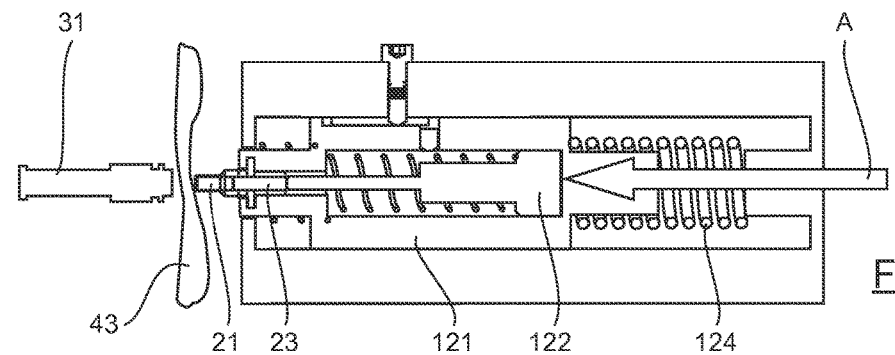

As illustrated in FIG. 12D, the user can then position the animal's ear 43 between the two arms of the applicator, and then actuate an unlocking button, which releases the compression exerted on the spring 124. The spring 124 relaxes, causing the main piston 121 and the secondary piston 122, which are still in the coupling position, to move towards the animal's ear. This action on an unlocking button gives rise to major acceleration of the main piston, converting the potential energy of the spring 124 into kinetic energy enabling the cutting element to perforate the animal's ear. The energy needed for shifting the main piston can thus be provided by the compression/decompression of the spring 124 rather than by the user.

According to the above-mentioned variant, the acceleration could be obtained by the pressure of the compressed air on the main piston, by means of a jack for example.

Figure 12E:
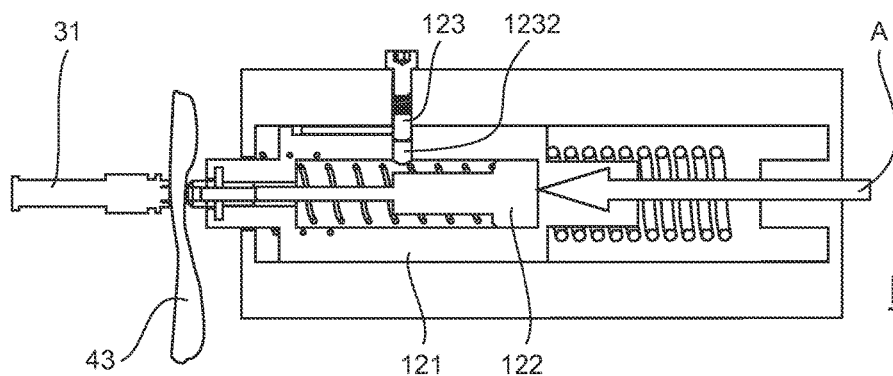

The main piston 121 and the secondary piston 122 continue their linked motions until the cutting element 21 perforates the animal's ear 43 as illustrated in FIG. 12E. The motion of the main piston 121 stops suddenly when the cutting element 21 abuts the collecting means, especially the tube top piece 32 and/or when the locking pin 123 penetrates the notch 1232 provided for this purpose.

This makes it possible to decouple the decoupling means and therefore to dissociate the motions of the main and secondary pistons.

Figure 12F:
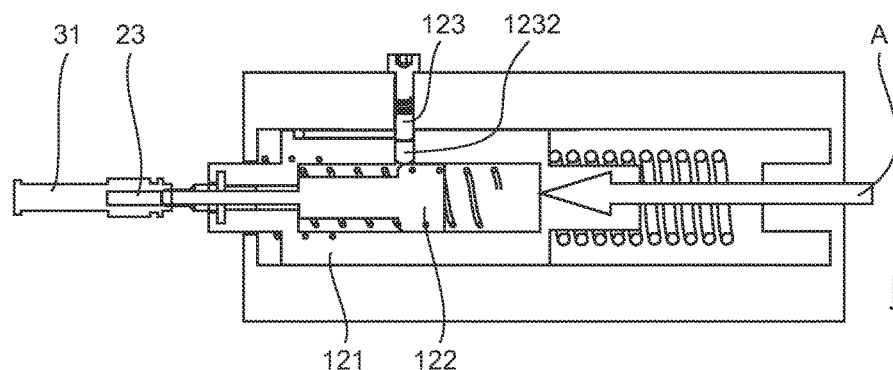

In other words, as illustrated in FIG. 12F, the sudden stopping of the motion of the main piston 121 when the cutting element 21 abuts the collection means and/or when the locking pin 123 penetrates the notch 1232 gives the secondary piston 122 energy, according to the law of conservation of quantities of motion, giving rise to a shift in translation of the secondary piston 122 propelling the pusher element towards the animal's ear. The pusher element thus extracts the cut-out sample from the cutting element, pushes it into the collecting tube and closes the collecting tube 31. In this embodiment, the secondary piston is therefore actuated solely by inertia.

Figure 12G:
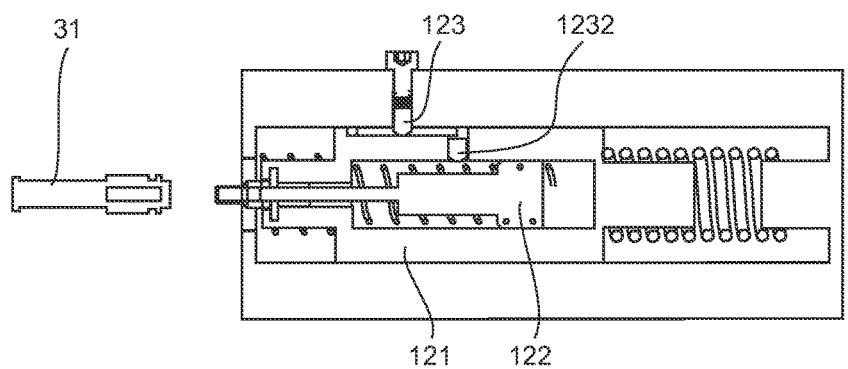
Figure 12H:
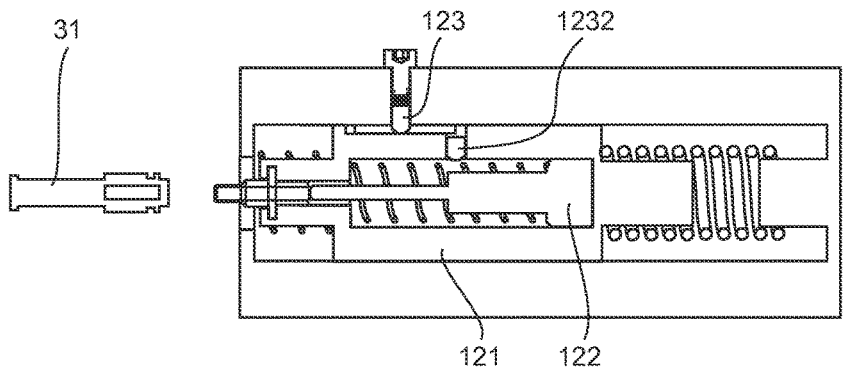

The secondary piston can especially take a specific shape as illustrated in the figures, including a swelling which pushes back the locking pin 123 out of the notch 1232 to release the motion of the main piston. Thus, as illustrated in FIGS. 12G and 12H, the main piston and then the secondary piston can resume their initial position after the releasing of the main piston, for example under the action of recall springs of low stiffness.

As described with reference to the other embodiments, it is possible for the user to eject the soiled cutting element for example by pulling on the main piston in a direction opposite the arrow A, with a part of the support of the cutting element abutting an element provided for this purpose on the body of the applicator.

The other characteristics and advantages described here above with reference to the other embodiments can also be applied to this embodiment and are therefore not repeated in detail herein.

D) Automatic Withdrawal of the Cutting Element

According to one particular embodiment of the invention, the cutting element can automatically resume its initial position once the sample has been cut out. This automatic withdrawal rapidly releases the animal's ear and prevents risks of cutting with a soiled cutting element, by protecting the cutting edge of the cutting element.

For example, this automatic withdrawal can occur when the cutting element abuts an abutment surface, such as the tube top piece, or when a locking pin penetrates a notch provided for this purpose according to the embodiment described here above.

In a first example as described here above with reference to FIGS. 12F to 12H, the automatic withdrawal of the cutting element can be obtained by using a specific shape for the secondary piston, comprising a swelling enabling the locking pin 123 to be pushed back out of the notch 1232. This releases the motion of the main piston and brings it into the idle position (thus protecting the cutting edge) and brings the secondary piston back into the idle position under the effect of recall springs of low stiffness.

Figure 13A:
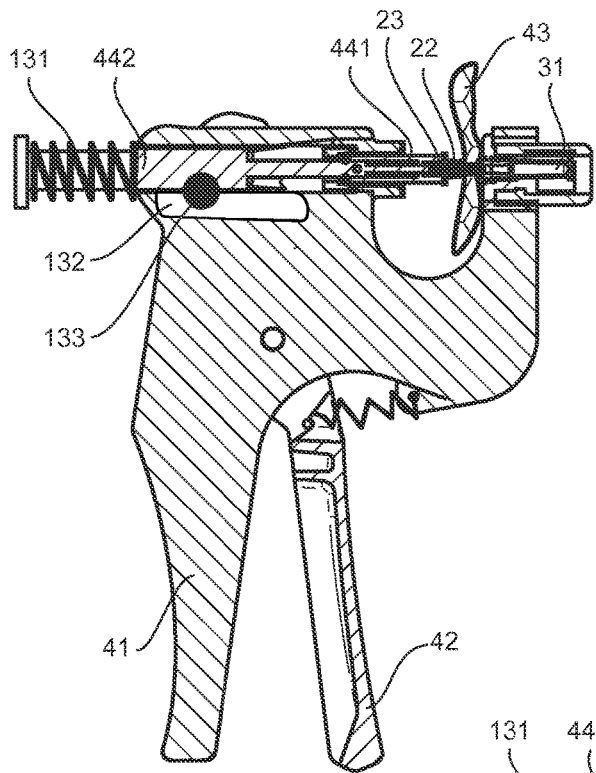
Figure 13B:
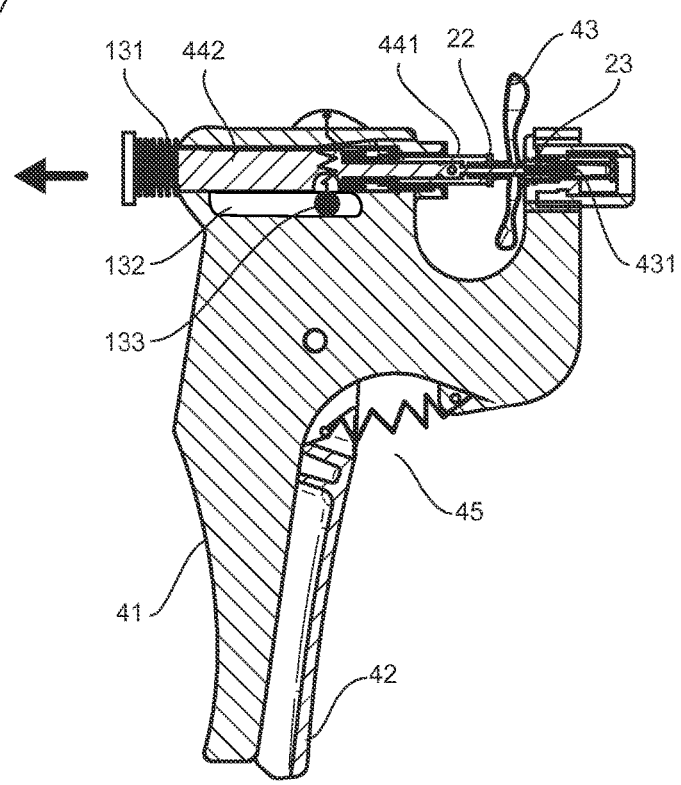

According to a second example, illustrated in FIGS. 13A and 13B, the automatic withdrawal of the cutting element is implemented by means of the combined use of a recall spring 131 linked to the means 442 for driving the pusher element, a transmission pin 133 linked to the driving means 442 and an aperture 132 in the body 41 of the applicator, in which the transmission pin 133 can move.

As described here above with reference to FIGS. 5A and 5B, the actuating of the lever 42 gives rise first of all to a simultaneous translation of the cutting element 21 and the pusher element 23 enabling the cutting element to cut out a sample of tissue until it abuts the flange of the tube top piece of the sampling tube 31. The continuance of this action on the lever 42 then gives rise to a translation of the pusher element 23 only, through the cutting element 21, thus giving rise to a compression of the recall spring 131 against the body of the applicator.

The shifting of the means 442 for driving the pusher element also drives a shifting of the transmission pin 133 along the aperture 132. In this variant, the aperture has a slope. Thus, the transmission pin 133 is kept in a notch provided for this purpose in the driving means 442 in a first stage and then, as and when the shift takes place along the aperture 132, the transmission pin 133 is released from the driving means 442. For example, the transmission pin 133 is held in a supporting position against the slope of the aperture 132 by means of a spring 134 fixedly joined to the lever 42.

Once the transmission pin 133 is released from the driving means 442, the recall spring 131 relaxes and draws back the means 442 for driving the pusher element and then the means 441 for driving the cutting element (linked by a spring 135) into their initial position.

Figure 14:
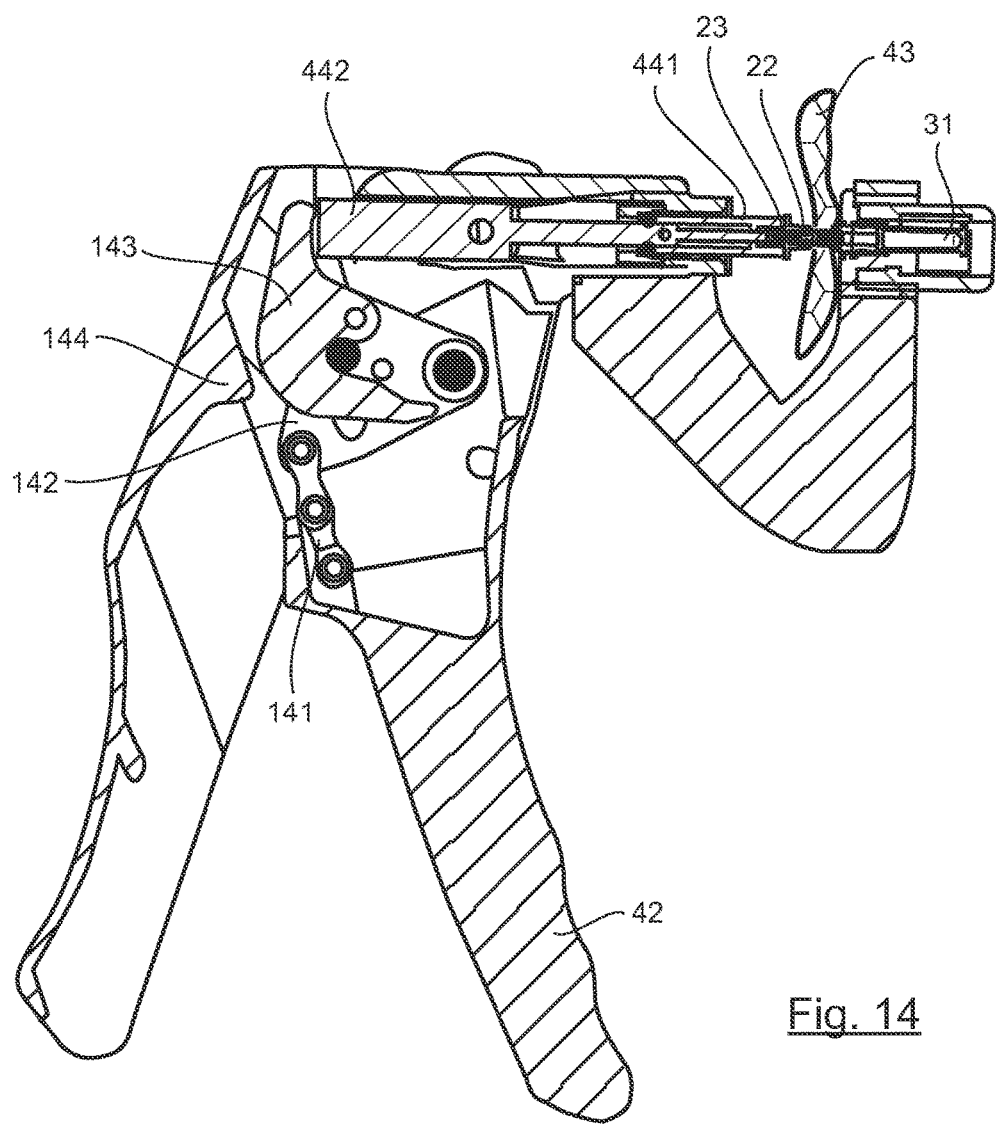

According to a third example, illustrated in FIG. 14, the automatic withdrawal of the cutting element is implemented by means of the combined use of a chain 141 formed by two links, at least one plate 142 and one cam 143 acting on the means 442 for driving the pusher element.

More specifically, the actuation of the lever 42 gives rise to a motion of the chain 141 transmitting the force needed for the rotation of the plate 142. The rotation of the plate 142 actuates the cam 143 which, in turn, actuates the means for driving the pusher element and the cutting element, simultaneously in a first stage and then dissociatedly in a second stage.

At the end of the travel of the lever 42, a stop 144 integrated into the body of the applicator obliges the chain 141 to get curved. It can then no longer transmit any force to the plate 142 which returns to its initial position under the effect of the recall springs. Subsequently, the cam 143 also returns to its initial position. The means 442 for driving the pusher element and the means 441 for driving the cutting element also return to their initial position since no force is any longer applied by the cam 143 to the driving means.

Figure 15:
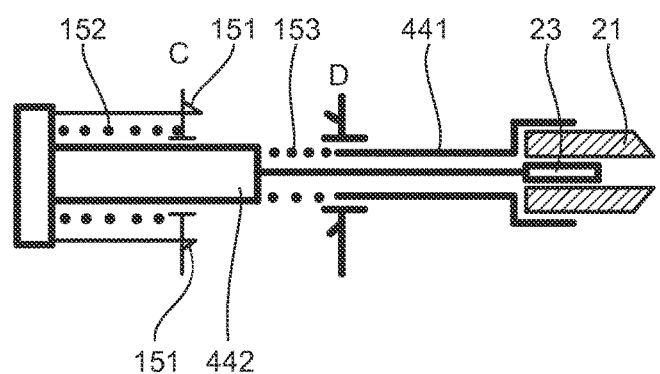

Finally, FIG. 15 illustrates a fourth example of the automatic withdrawal of the cutting element, implementing a hook-based mechanism.

In this example, the means 442 for driving the pusher element are provided with hooks 151 used to prime the applicator and for the automatic withdrawal of the cutting element once the collecting operation is terminated.

The priming of the applicator is done for example by pushing the means 442 for driving the pusher element until the hooks 151 hook an element C corresponding to the applicator, leading to the compression of a recall spring 152 between the base of the means 442 for driving and the hooked element C.

The shifting of the hooked element C and of the means 442 for driving the pusher element, by actuation of the applicator for example, gives rise first of all to a simultaneous translation of the cutting element 21 and the pusher element 23 (the means 441 for driving the cutting element being linked to the means 442 for driving the pusher element by means of a spring 153). When the cutting element abuts the flange of the tube top piece of the sampling tube, the spring 153 gets compressed and only the pusher element 23, pushed by the driving means 442, continues its course through the cutting element 21.

The compression of the spring 153 brings the hooked element C into contact with a corresponding "unhooking" element D, enabling the hooks 151 to be released from the hooked element C. Once the hooks 151 of the driving means 442 are unlocked, the recall spring 152 relaxes and recalls the means 442 for driving the pusher element and then the means 441 for driving the cutting element (by means of the spring 153) to their initial position.

It must be noted that these four examples of implementation are described in the case where the applicator works with collecting means comprising both a cutting element and a pusher element. These mechanisms could of course be implemented in a "classic" applicator working with collecting means comprising a simple punch not combined with a pusher element.

E) Variants

Whatever the embodiment envisaged, the tool for collecting according to the invention imparts a motion of translation to the cutting and pusher elements along a same direction, the two motions being linked in a first stage and delinked in a second stage.

It may be recalled that these two stages correspond to a single action by the user on the tool for collecting, the first stage corresponding to a first portion of the course of the lever between an initial position and an intermediate position, defining a coupling position, and the second stage corresponding to a second portion of the course of the lever between the intermediate position and a final position, defining a decoupling position.

Other coupling means can also be envisaged provided that they enable a dual parallel motion of translation of the cutting element and the pusher element, simultaneously in a first stage and then dissociatedly thereafter, so that the cutting element cuts the tissues of the animal before the pusher element pushes the sample thus cut.

In the embodiment described, the tool for collecting is actuated by hand. Naturally, it could be actuated by means of electrical, pneumatic or other forms of power.

Furthermore, in the embodiment described, the lever is mobile in rotation between the initial, intermediate and final positions. In one variant, not shown, the lever can be mobile in translation between these different positions.

According to yet another embodiment, the tool for collecting can place an identifying tag (visual and/or electronic), simultaneously with the collecting of the sample. Advantageously, this identifying mark carries an identifier linked to an identifier of the collecting and/or storage means.

The invention claimed is:

1. A tool for collecting a sample of animal tissue, comprising a first arm designed to cooperate with at least one cutting element designed to cut out a sample of animal tissue and one pusher element that is mobile relative to said cutting element and designed to push said sample of animal tissue into a storage element after cutting, and a second arm designed to cooperate with said storage element, the first arm comprising:
 a primary pin configured to transmit a motion of translation to said cutting element along an axis of translation in a direction of a sample of animal tissue, enabling the cutting element to cut out the sample of animal tissue disposed between the first arm and the second arm, until the cutting element abuts the storage element;
 a secondary pin configured to transmit a motion of translation to said pusher element along said axis of translation in the direction of said sample of animal tissue, enabling the pusher element to push the sample up to the storage element;
 at least one mobile coupling element; and
 a housing;
 wherein said primary pin and said secondary pin are configured to be mobile between a coupling position and a decoupling position;
 wherein the movement of said cutting element and the movement of said pusher element are linked together in the coupling position, said at least one mobile coupling element being configured to be held within the housing in said coupling position;
 wherein the movement of said cutting element and the movement of said pusher element are disassociated and move independently of each other in the decoupling position, said at least one mobile coupling element being configured to be released in said decoupling position; and
 wherein said at least one mobile coupling element is a ball.

2. The tool according to claim 1, further comprising:
 at least one hinged grip forming a lever that is mobile on a predetermined course comprising a first movement position and a second movement position;
 wherein said lever is configured to move the primary pin and the secondary pin from said coupling position on said first movement position to said decoupling position on said second movement position.

3. The tool according to claim 1, wherein said secondary pin comprises at least one groove, where said housing faces said groove in said coupling position.

4. The tool according to claim 3, wherein said housing is a through aperture and said ball is held in said housing by means of a sliding part, where said sliding part is shaped to hold said ball in said groove in said coupling position and to release said ball from said groove in said decoupling position.

5. The tool according to claim 4, wherein:
said sliding part is a sleeve comprising at least two sections of distinct diameters; and
said ball being held by the section having a smaller diameter and being released by the section having a greater diameter.

6. The tool according to claim 4, wherein said sliding part is connected to the secondary pin by a slide spring, said slide spring being in an idle state in said coupling position and in a compressed state in said decoupling position.

7. The tool according to claim 1, further comprising an ejection member configured to eject said cutting element.

8. A tool for collecting a sample of animal tissue, comprising a first arm designed to cooperate with at least one cutting element designed to cut out a sample of animal tissue and one pusher element that is mobile relative to said cutting element and designed to push said sample of animal tissue into a storage element after cutting, and a second arm designed to cooperate with said storage element,
the first arm comprising:
a primary pin configured to transmit a motion of translation to said cutting element along an axis of translation in a direction of a sample of animal tissue, enabling the cutting element to cut out the sample of animal tissue disposed between the first arm and second arm, until the cutting element abuts the storage element;
a secondary pin configured to transmit a motion of translation to said pusher element along said axis of translation in the direction of said sample of animal tissue, enabling the pusher element to push the sample up to the storage element;
at least one mobile coupling element; and
a housing;
wherein said primary pin and said secondary pin are configured to be mobile between a coupling position and a decoupling position;
wherein the movement of said cutting element and the movement of said pusher element are linked together in the coupling position, said at least one mobile coupling element being configured to be held within the housing in said coupling position;
wherein the movement of said cutting element and the movement of said pusher element are disassociated and move independently of each other in the decoupling position, said at least one mobile coupling element being configured to be released in said decoupling position; and
wherein said at least one mobile coupling element is a ball which is held in said housing by means of a sleeve comprising at least two sections of distinct diameters, said ball being held in a groove of the secondary pin in the section having a smaller diameter in said coupling position and being released from said groove in the section having a greater diameter in said decoupling position.

* * * * *